(12) United States Patent
Lowe

(10) Patent No.: US 6,572,571 B2
(45) Date of Patent: Jun. 3, 2003

(54) LIMB STABILIZER

(76) Inventor: Richard Dean Lowe, 2324 Raintree Dr., Brea, CA (US) 92821

( * ) Notice: Subject to any disclaimer, the term of this patent is extended or adjusted under 35 U.S.C. 154(b) by 0 days.

(21) Appl. No.: 09/939,465

(22) Filed: Aug. 25, 2001

(65) Prior Publication Data

US 2002/0026135 A1 Feb. 28, 2002

Related U.S. Application Data

(60) Provisional application No. 60/229,093, filed on Aug. 31, 2000.

(51) Int. Cl.$^7$ .................................................. A61F 5/00
(52) U.S. Cl. ............................... 602/5; 602/12; 602/23; 602/26
(58) Field of Search ......................... 602/56, 72, 74, 602/5–6, 12, 16, 20, 23, 25, 10, 26–29; 36/110, 117, 120, 140

(56) References Cited

U.S. PATENT DOCUMENTS

| | | | | | |
|---|---|---|---|---|---|
| 3,580,248 A | * | 5/1971 | Larson | ........................ | 602/12 |
| 3,955,565 A | * | 5/1976 | Johnson, Jr. | .................. | 128/89 |
| 4,538,595 A | * | 9/1985 | Hajianpour | ................... | 601/33 |
| 5,242,379 A | * | 9/1993 | Harris et al. | ................... | 602/27 |
| 5,707,347 A | * | 1/1998 | Bixler | ......................... | 602/26 |
| 5,853,380 A | * | 12/1998 | Miller | .......................... | 602/27 |
| 6,117,097 A | * | 9/2000 | Ruiz | ............................ | 602/26 |
| 6,228,044 B1 | * | 5/2001 | Jensen et al. | ................. | 602/27 |
| 6,280,446 B1 | * | 8/2001 | Blackmore | ................... | 606/56 |

* cited by examiner

*Primary Examiner*—Nicholas D. Lucchesi
*Assistant Examiner*—Lalita M. Hamilton
(74) *Attorney, Agent, or Firm*—Jerry R. Potts

(57) ABSTRACT

A stabilizer for stabilizing a limb of an animal, an elongated trough-shaped base for supporting the limb, a trough-shaped extension, integrally connected to the base, and extending therefrom at an acute angle relative to the axis of the base. An elongated trough-shaped cover is connectable to the base. Additionally, a curved, trough-shaped support and means for fastening the support to the base are provided.

19 Claims, 2 Drawing Sheets

LIMB STABILIZER

CROSS REFERENCE TO RELATED APPLICATIONS

The present patent application is a continuation-in-part patent application of Ser. No. 60/229,093, titled "Stabilizer", filed Aug. 31, 2000. Said application is incorporated by reference as though set forth in full herein.

BACKGROUND OF THE INVENTION

The present invention relates generally to medical devices and, more particularly, to devices for stabilizing limbs of animals during intravenous (IV) fluid delivery.

It is well recognized in the practice of veterinary medicine that delivery of intravenous fluids to an injured animal, especially in cases of burns or injury, can be a life saving process. Often, the fluids are administered through the cephalic vein, a large superficial vein in the forelimb running from the paw to the shoulder. The injection site is generally on the anterior surface of the limb, between the paw and the elbow joint.

In some cases, controlling the animal during the IV fluid delivery is a daunting task. Problems can be encountered when a frightened or uncomfortable animal moves the limb in which the IV needle has been injected, thereby dislodging the needle and interrupting fluid delivery. In other cases, after injection, the animal brings the forelimb up against the chest thereby occluding the IV catheter and blocking fluid flow.

Conventional techniques, such as taping the limb to a flat surface for example, are sometimes ineffective and can lead to increased discomfort in the animal. In addition, it is sometimes necessary for two animal handlers to be required in an attempt to stabilize the animal's limb.

In view of the foregoing, it is desirable to have a limb stabilizer, usable effectively by a single animal handler, that would enable effective IV fluid delivery into the vein of an animal, while substantially reducing the capability of the animal to dislodge the IV needle or to occlude the catheter. Additionally, it would be highly advantageous if the limb stabilizer could prevent occlusion of the IV catheter, in spite of limb movements by the catheterized animal.

Preferably, such a limb stabilizer would be low in cost and constructed of readily available material. Desirably, the limb stabilizer would be adjustable so as to suit a variety of limb sizes.

SUMMARY

According to the present invention, there is provided a stabilizer for stabilizing a limb of an animal, the stabilizer including an elongated trough-shaped base for supporting the limb, a trough-shaped extension, integrally connected to the base, and extending therefrom at an acute angle relative to the axis of the base. This angle is between about 35° and about 60° and, preferably the acute angle is about 45°.

The base includes a first edge and a second edge. An elongated trough-shaped cover is hingedly connected to the base along the base first edge. Fastening means, disposed on the cover and at the base second edge, attach the cover to the base. Additionally, a curved, trough-shaped support and means for fastening the support to the base for help to stabilize the limb are provided.

In further detail, the limb stabilizer includes an elongated trough-shaped base for supporting the limb and a trough-shaped extension, integrally connected to the base, and extending therefrom at an acute angle, relative to the axis of the base. An elongated trough-shaped cover is provided along with means for fastening the cover to the base. In addition, a curved, trough-shaped support and means for fastening the support to the base, for helping to stabilize the limb, are provided. The base, cover and support are each lined with a pliable foam sheet for adding to the comfort of the animal being treated.

In a presently preferred embodiment, the limb stabilizer base includes a first edge and a second edge and the elongated trough-shaped cover is hingedly connected to the base along the first edge. The means for fastening the cover to the base is disposed on the cover and at the base second edge The fastening means includes a strap and a strap-retaining buckle. In another embodiment of the invention, the fastening means includes a strap of pile material and a tab of hook material adapted for receiving and holding the pile strap.

The present invention also provides a method of stabilizing a limb of an animal, the limb having an anterior surface and a posterior surface. The method comprises the steps of providing an elongated trough-shaped base for supporting the limb, providing a trough-shaped extension, integrally connected to the base, and extending coaxially therefrom at an acute angle relative to the axis of the base, and providing an elongated trough-shaped cover. In use, the base is placed along the limb posterior surface and the cover is attached to the base. A curved, trough-shaped support is provided and it is fastened to the base for helping to stabilize the limb.

In a presently preferred embodiment, there is a step of providing an opening in the extension for engaging the elbow of the animal. This step orients the stabilizer relative to the limb. In addition, it enables ready installation of the stabilizer on the limb as the elbow rests at least partially within the opening.

The present invention affords several advantages. By virtue of the method of attaching the device to the limb of the animal, it makes it possible for a single handler to accomplish the task. In addition, it reduces substantially the likelihood of IV tube occlusion or removal as a result of animal movement. The stabilizer is adjustable, thereby accommodating limbs of varying sizes. Further, the limb stabilizer is low in cost and constructed of readily available materials.

In summary, a limb stabilizing device embodying the invention is easy to install by a single individual, mechanically simple, adjustable, low in cost and easy to remove.

Other aspects and advantages of the present invention will become apparent from the following detailed description, taken in conjunction with the accompanying drawings, illustrating by way of example the principles of the invention.

DETAILED DESCRIPTION

Figure 1:
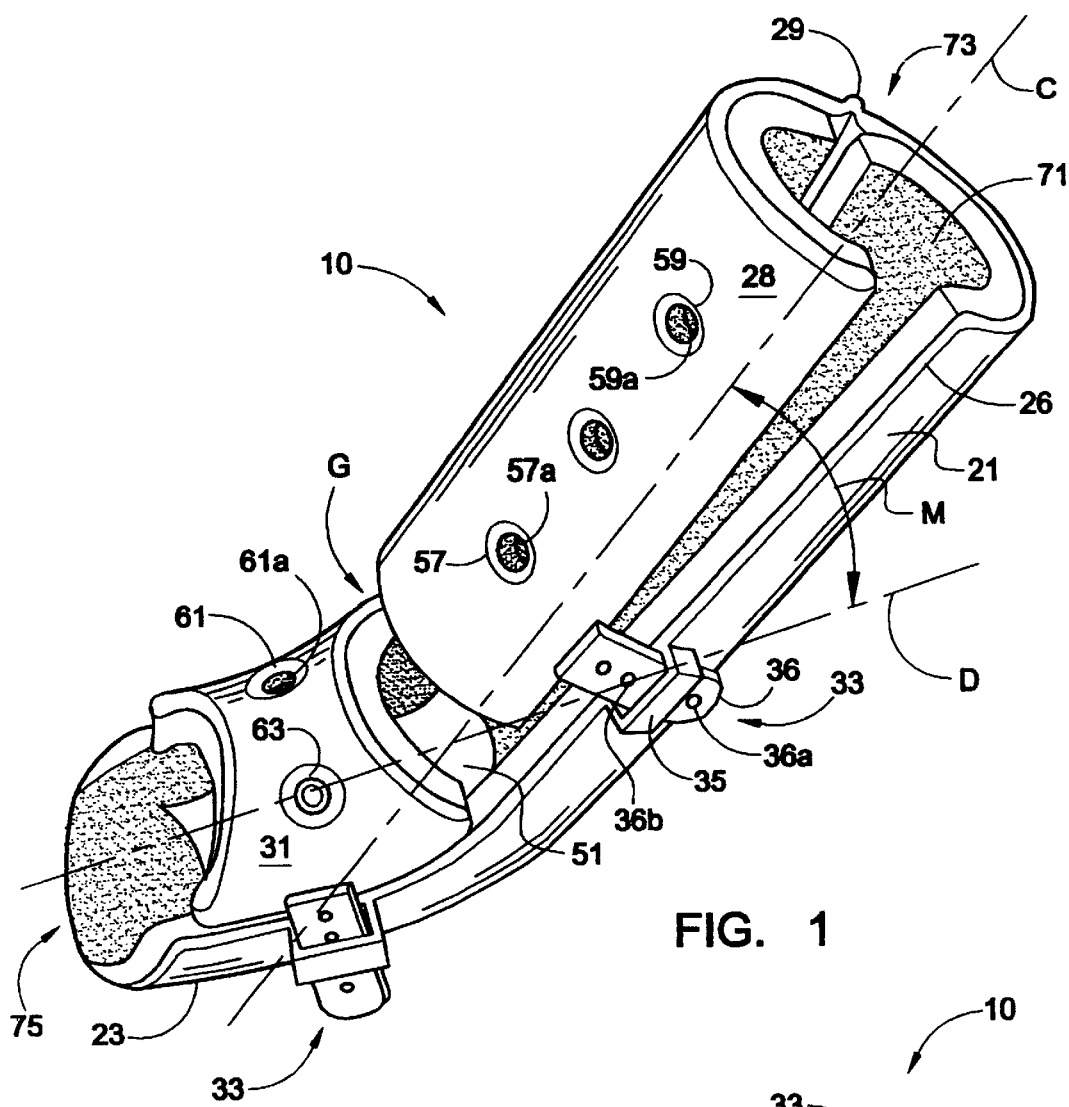
FIG. 1 is a perspective view of a limb stabilizer that is constructed according to the present invention.
Figure 2:
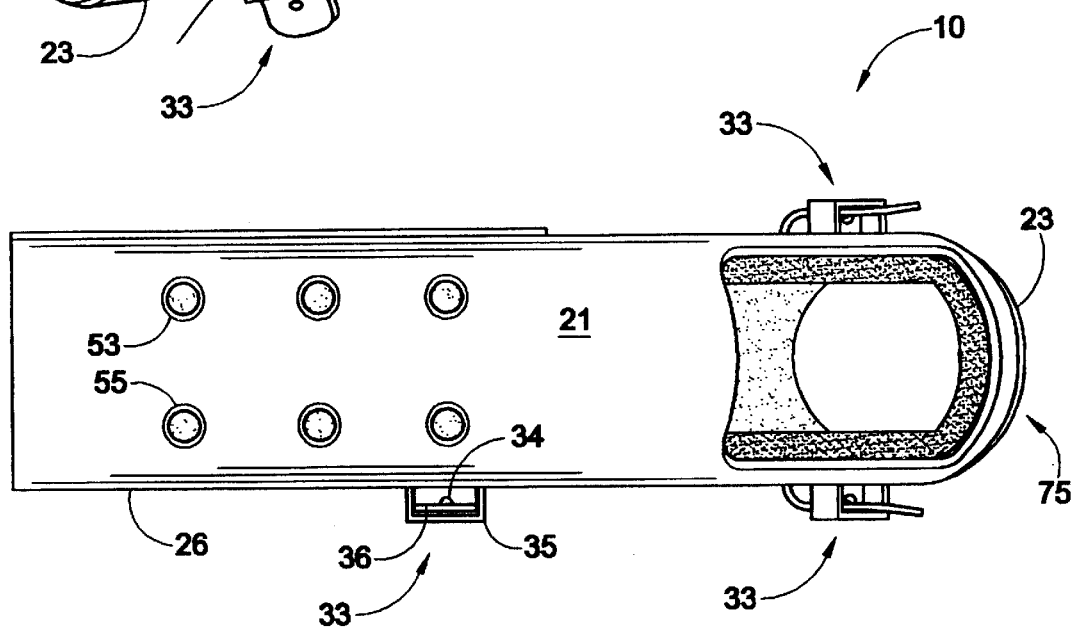
FIG. 2 is a bottom plan view of the limb stabilizer of FIG. 1.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

In the following detailed description and in the several figures of the drawings, like elements are identified with like reference numerals.

As shown in the drawings for purposes of illustration, the invention is embodied in a novel limb stabilizer for preventing needle removal or catheter occlusion during IV fluid delivery.

Referring now to the drawings and more particularly, to FIGS. 1–4 thereof, there is shown a limb stabilizer 10 that is constructed according to the present invention. The stabilizer includes an elongated trough-shaped base 21, arcuate in cross section, that in use is disposed along the posterior surface of the animal limb, distal to the elbow. A trough-shaped extension 23 is integrally connected to the base 21, extending therefrom at an acute angle. As best shown in FIG. 1 the axis C of the base 21 forms an angle M with the axis D of the trough-shaped extension 23. The angle M may range from about 35° to about 60° and, preferably is about 45°.

When the term "cross section" is used herein, it refers to a section taken along a line perpendicular to either the axis C or the axis D.

The extension 23 has an elongated opening 51 formed therein. In use of the stabilizer 10, when the base is disposed along the posterior surface of the limb, the extension supports the posterior surface of the limb above the elbow and the elbow rests, at least partially, within the opening 51. In this manner, the stabilizer 10 can be readily secured on the limb while movement relative to the limb is minimized.

A curved, trough-shaped support 31, also arcuate in cross section, and separate from the base 21 and the cover 28, is provided. The support 31 is gently radiused to follow generally the contour of the extension 23. The support 31 is reversibly attachable to the elongated trough-shaped extension 23 by a pair of oppositely disposed fastening means discussed more fully below.

Figure 3:
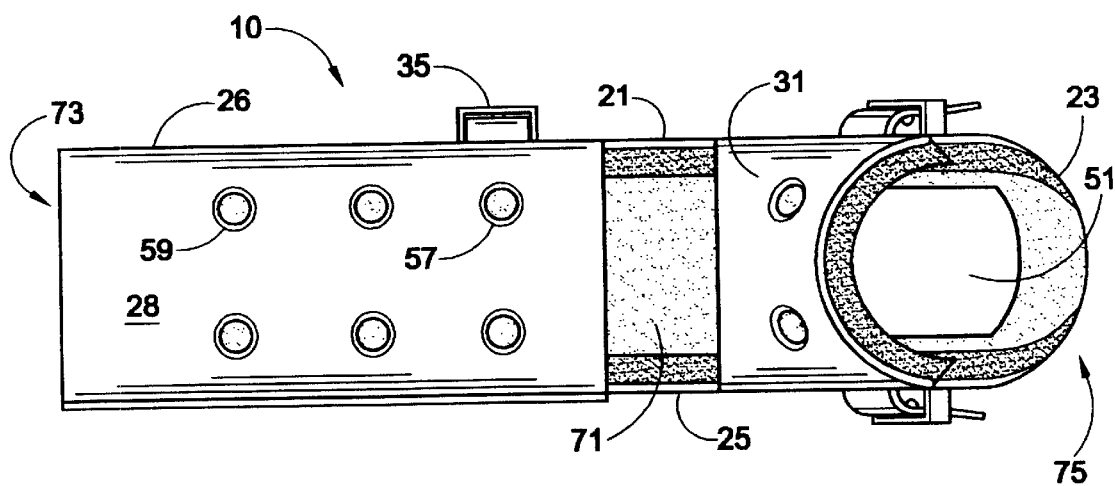
FIG. 3 is a top view of the limb stabilizer of FIG. 1.
Figure 4:
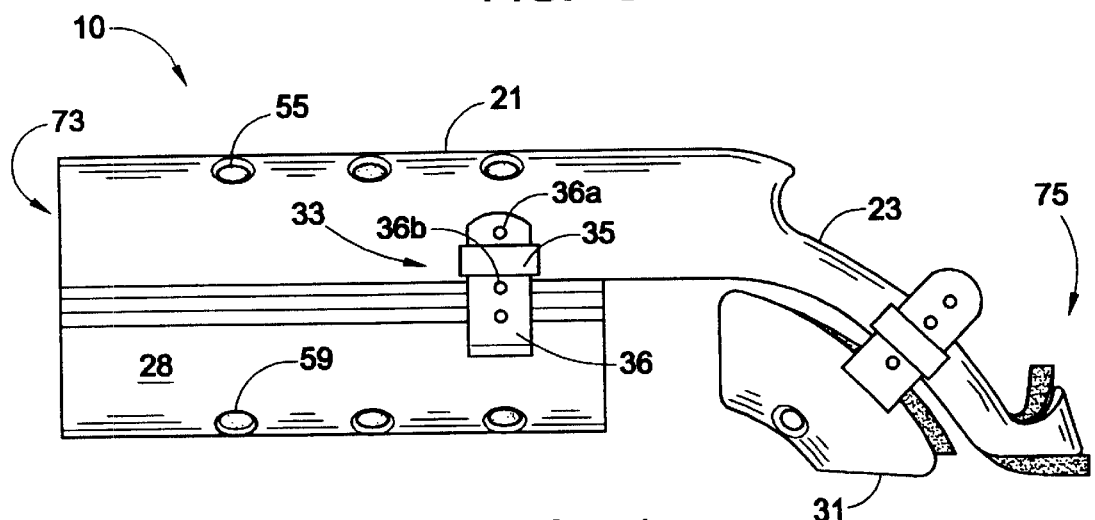
FIG. 4 is a left side elevational view of the limb stabilizer shown in FIG. 1.

As shown in FIGS. 1 and 3, the support 31 is generally trough-shaped in transverse cross section about an axis lying in planes defining said cross section and curved about an axis substantially perpendicular to said first mentioned axis.

The base 21 includes a first edge 25 and an oppositely disposed second edge 26. An elongated trough-shaped cover 28, arcuate in cross section, is hingedly attached to the base 21 along an integrally formed living hinge 29.

Fastening means, generally indicated by the reference numeral 33, are utilized for adjustable attachment of the cover 28 to the base 21. In a similar manner, fastening means 33 are located on either side of the support 31 for adjustable attachment of the support to the base 21. In each case, the fastening means 33 include a strap 36 and a strap-receiving buckle 35. It will be noted that the strap 36 includes a plurality of openings, such as the openings 36a and 36b, to enable receipt of the strap 36 by a stud 34 disposed within the buckle 35 and to enable adjustment of the diameter of the limb stabilizer 10.

As an aid in providing comfort to the animal being treated the base 21, and cover 28 are lined by a pliable foam lining 71. In a similar manner, the trough-shaped support 31 includes a pliable foam lining.

In order to lighten the weight of the limb stabilizer 10 and provide ventilation of the limb, a plurality of openings such as the openings 53 and 55 in the base 21, 57 and 59 in the cover 28, and 61 and 63 in the support 31 is provided. Openings in the underlying pliable foam lining 71 correspond to the aforementioned openings in the base 21, cover 28 and support 31. That is, for example openings 57a and 57b correspond, respectively, to the holes 57 and 59 in the cover 28 while openings 61 and 63 correspond, respectively, to openings 61 and 63 in the support 31.

In use of the limb stabilizer 10, after a needle attached to an IV catheter has been inserted into the cephalic vein of the animal (needle, catheter and limb not shown), the limb of the animal is placed in the base 21 and the support 31 is attached via the fastening means 33 to the base. The base 21 includes a proximal end 75 and a distal end 73 (with respect to the limb of the animal) and the catheter may be routed under the cover 28 to exit the stabilizer 10 at either the proximal end 75 or the distal end 73. The cover 28 is attached to the base 21 by means of the fastening means 33 above described.

When the elements 28 and 31 are attached to the base 21, a gap G is provided. The gap enables clearance between the elements 28 and 31. If desired, the catheter may be routed from under the cover 28 to exit the limb stabilizer 10 through the gap G.

Figure 5:
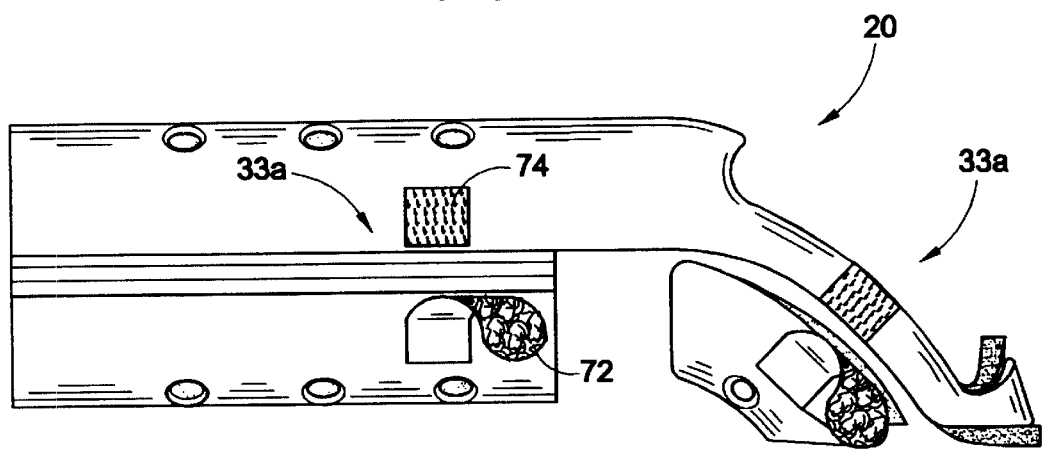
FIG. 5 is a perspective view of another embodiment of the limb stabilizer of the present invention showing another technique of attaching one portion of the stabilizer to another.

An embodiment of the invention having certain additional features is shown in FIG. 5. Here, a limb stabilizer 20 is depicted. This embodiment is identical in all respects to the limb stabilizer 10, except with respect to fastening means, having structural elements that are identical in structure and function to counterparts in the limb stabilizer 10. For this reason, the counterparts in the limb stabilizer 20 will not be described in any detail, their description being incorporated herein by reference.

Where the stabilizer 10 utilizes the fastening means 33 for attachment of elements, the stabilizer 20 utilizes fastening means generally indicated in FIG. 5 by the reference 33a. Here, the fastening means 33a includes a strap 72 having hooks thereon disposed engagement of a tab 74 containing pile material.

From the foregoing it will be appreciated that the limb stabilizer provided by the invention provides an efficient technique for prevention of unwanted needle removal or catheter occlusion during IV fluid administration. The limb stabilizer is mechanically simple, easy to assemble and easy to remove after completion of the fluid delivery process.

Those skilled in the art will recognize that the present invention is useful as a splint for stabilization of a fractured, burned or lacerated limb. Therefore, as the term "limb stabilizer" is used herein, it is intended to cover such applications and not be limited only to IV catheterization applications.

It will be evident that there are additional embodiments and applications that are not disclosed in the detailed description but which clearly fall within the scope of the present invention. The specification is, therefore, intended not to be limiting, and the scope of the invention is to be limited only by the following claims.

What is claimed is:

1. A limb stabilizer, comprising:
   an elongated trough-shaped base for supporting the limb;
   a trough-shaped extension, integrally connected to said base, and extending therefrom at an acute angle relative to the axis of said base;

an elongated trough-shaped cover;

means for fastening said cover to said base;

a support; and means for fastening said support to said base for helping to stabilize the limb, wherein said cover and said support are in separated relationship when said cover and said support are fastened to said base and said support is generally trough-shaped in transverse cross section about an axis lying in planes defining said cross section and curved about an axis substantially perpendicular to said first mentioned axis.

2. The limb stabilizer according to claim 1, wherein said base includes a first edge and a second edge and said elongated trough-shaped cover is hingedly connected to said base along said first edge.

3. The limb stabilizer according to claim 1, wherein said means for fastening said cover to said base is disposed on said cover and at said base second edge.

4. The limb stabilizer according to claim 1, wherein said acute angle is between about 35° and about 60°.

5. The limb stabilizer according to claim 1, wherein said acute angle is about 45°.

6. The limb stabilizer according to claim 1, wherein said means for fastening said cover to said base includes at least one strap and one buckle.

7. The limb stabilizer according to claim 1, wherein said means for fastening said cover to said base includes a plurality of straps and buckles.

8. The limb stabilizer according to claim 1, wherein said means for fastening said curved support to said base includes at least one strap and one buckle.

9. The limb stabilizer according to claim 1, wherein said means for fastening said curved support to said base includes a plurality of straps and buckles.

10. The limb stabilizer according to claim 1, wherein said means for fastening said cover to said base includes at least one strap having pile disposed thereon and another strap having hooks disposed thereon.

11. The limb stabilizer according to claim 1, wherein said means for fastening said cover to said base includes a plurality of straps having pile disposed thereon and a plurality of straps having hooks disposed thereon.

12. The limb stabilizer according to claim 1, wherein said means for fastening said curved support to said base includes at least one strap having pile disposed thereon and at least one strap having hooks disposed thereon.

13. The limb stabilizer according to claim 1, wherein said means for fastening said curved support to said base includes a plurality of straps having pile disposed thereon and a plurality of straps having hooks disposed thereon.

14. The limb stabilizer according to claim 1, wherein said base, said cover and said trough-shaped extension each has a plurality of openings therein formed.

15. The limb stabilizer according to claim 1, wherein each one of said base, said cover and said trough-shaped extension includes a pliable lining.

16. A method of stabilizing a limb of an animal, the limb having an anterior surface and a posterior surface, comprising the steps of:

providing an elongated trough-shaped base for supporting the limb;

providing a trough-shaped extension, integrally connected to said base, and extending coaxially therefrom at an acute angle relative to the axis of said base;

providing a support;

fastening said support to said base for helping to stabilize the limb, wherein said cover and said support are in separated relationship when said cover and said support are fastened to said base and said support is generally trough-shaped in transverse cross section about an axis lying in planes defining said cross section and curved about an axis substantially perpendicular to said first mentioned axis;

placing said base along said limb posterior surface;

fastening said support to said base;

providing a curved, trough-shaped cover; and fastening said cover to said base for helping to stabilize the limb.

17. The method according to claim 16, including the steps of providing an opening in said extension for engaging the elbow of the animal and installing said base on said limb so that said elbow rests at least partially within said opening.

18. The limb stabilizer according to claim 16, wherein said providing a trough-shaped extension step includes integrally connecting said extension to said base whereby said base and said extension form an angle of between about 35° and about 60°.

19. The limb stabilizer according to claim 16, wherein said providing a trough-shaped extension step includes integrally connecting said extension to said base whereby said base and said extension form an angle of about 45°.

* * * * *